United States Patent [19]

Köppe et al.

[11] 4,016,286
[45] Apr. 5, 1977

[54] PHARMACEUTICAL COMPOSITIONS CONTAINING A 1-PHENOXY-2-HYDROXY-3-ALKYNYLAMINO-PROPANE AND THEIR USE AS ADRENOLYTICS AND HYPOTENSIVES

[75] Inventors: Herbert Köppe; Werner Kummer; Helmut Stähle; Gojko Muacevic, all of Ingelheim am Rhein, Germany

[73] Assignee: Boehringer Ingelheim GmbH, Ingelheim am Rhein, Germany

[22] Filed: Sept. 23, 1975

[21] Appl. No.: 615,913

Related U.S. Application Data

[62] Division of Ser. No. 444,713, Feb. 22, 1974, Pat. No. 3,925,446.

[30] Foreign Application Priority Data

Feb. 28, 1973  Germany .......................... 2309887
Jan. 26, 1974  Germany .......................... 2403809

[52] U.S. Cl. .......................... 424/304; 260/405 D; 260/465 E; 424/361; 424/362
[51] Int. Cl.² .......................... A61K 31/135
[58] Field of Search .......................... 424/304

[56] References Cited
UNITED STATES PATENTS 3,459,782  8/1969  Koppe et al. .......................... 260/465
3,541,130  11/1970  Koppe et al. .......................... 260/465
3,712,927  1/1973  Howe et al. .......................... 260/465 X

*Primary Examiner*—Albert T. Meyers
*Assistant Examiner*—Vera C. Clarke
*Attorney, Agent, or Firm*—Hammond & Littell

[57] ABSTRACT

Pharmaceutical compositions containing as an active ingredient a racemic or optically active compound of the formula

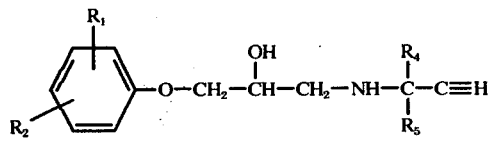

wherein
 $R_1$ is $-(CH_2)_x-CN$, where X is 0, 1, 2 or 3,
 $R_2$ is hydrogen, halogen or $-NH-CO-NHR$, where R is lower alkyl,
 $R_4$ is alkyl of 1 to 3 carbon atoms, and
 $R_5$ is alkyl of 1 to 3 carbon atoms or, together with $R_4$, $-(CH_2)_p-$ where $p$ is 4, 5 or 6, or a physiologically compatible acid addition salt thereof; and a method of using the same as adrenolytics and hypotensives.

12 Claims, No Drawings

PHARMACEUTICAL COMPOSITIONS CONTAINING A 1-PHENOXY-2-HYDROXY-3-ALKYNYLAMINO-PROPANE AND THEIR USE AS ADRENOLYTICS AND HYPOTENSIVES

This is a division of copending application Ser. No. 444,713 filed Feb. 22, 1974, now U.S. Pat. No. 3,925,446 granted Dec. 9, 1975.

This invention relates to novel pharmaceutical compositions containing as an active ingredient a 1-phenoxy-2-hydroxy-3-alkynylamino-propane or a physiologically compatible acid addition salt thereof, as well as to a method of using the same as adrenolytics and hypotensives.

More particularly, the present invention relates to novel pharmaceutical dosage unit compositions consisting essentially of an inert pharmaceutical carrier and an effective adrenolytic or hypotensive amount of a racemic or optically active compound of the formula

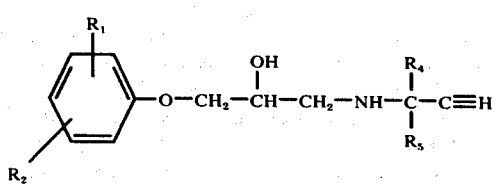

wherein $R_1$ is —$(CH_2)_x$—CN, where X is 0, 1, 2 and 3, $R_2$ is hydrogen, halogen or —NH—CO—NHR, where R is lower alkyl, $R_4$ is alkyl of 1 to 3 carbon atoms, and $R_5$ is alkyl of 1 to 3 carbon atoms or, together with $R_4$, —$(CH_2)_p$— where $p$ is 4, 5 6, or a physiologically compatible acid addition salt thereof.

The compounds of the formula I may be produced in a number of ways, among which the following are representative:

a. Reacting a compound of the formula

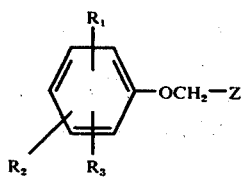

where $R_1$ to $R_3$ are defined as in formula I and Z is

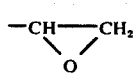

or —CHOH—$CH_2$—Hal (Hal = halogen), with an amine of the formula

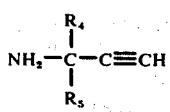

where $R_4$ and $R_5$ have the meanings indicated in formula I;

b. Cleaving an easily removable protective group off compounds of the formula

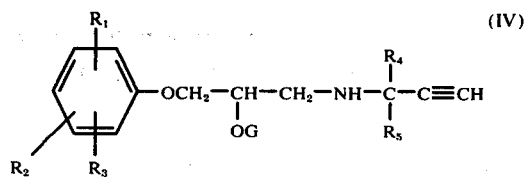

where $R_1$ to $R_5$ are defined as in formula I and G is an easily hydrogenolytically removable group, for example, an acyl or an acetal group.

c. Cleaving a protective group off a compound of the formula

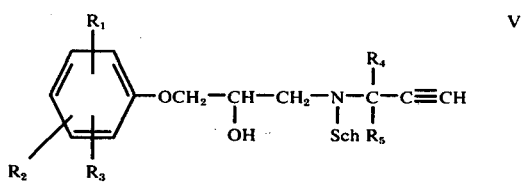

where $R_1$ to $R_5$ are defined as in formula I and Sch is an easily removable protective group, for example, an acyl group or the carbobenzoxy group;

d. Hydrolyzing an oxazolidine derivative of the formula

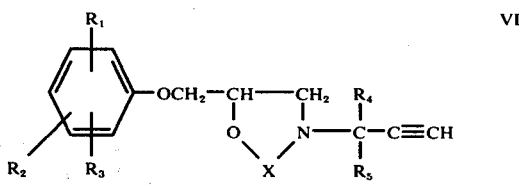

where $R_1$ to $R_5$ are defined as in formula 1, and X represents —CO—, —$CH_2$— or a —CH-lower alkyl group, for example, with sodium hydroxide or potassium hydroxide solution in water or in an alcohol/water mixture.

In addition, other processes for the production of compounds of formula I are possible, such as converting a compound having already the 3-alkynylamino-propanol-2 side chain, but not having one of the substituents $R_1$, $R_2$ or $R_3$ on the phenyl ring and in place thereof another substituent convertible to the desired substituent, to the desired substituent $R_1$, $R_2$ or $R_3$ by conventional methods.

e. Converting compounds of formula VIIa

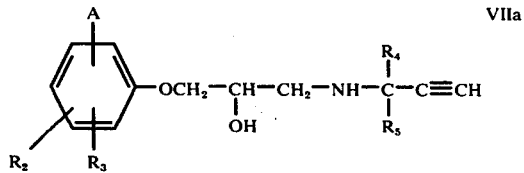

where $R_2$ to $R_5$ are defined as in formula I and A is a group convertible in line with conventional methods, such as the —$CONH_2$ or —$COOR_6$ group (whereby $R_6$ is defined as in formula I), an alkoxy, O-acyl or NO₂ group, for compounds of general formula VIIb

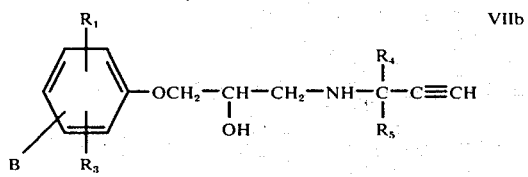

where $R_1$ and $R_3$ to $R_5$ are defined as in formula I and B is a group convertible into $R_2$ in line with conventional methods, into compounds of formula I, using the method required in each case (splitting off water, reducing, saponifying, cleaving an ether, alkylating).

Furthermore, the following process is suitable for producing compounds of general formula I, where $R_2$ or $R_3$ is a halogen atom:

f. Introducing a halogen atom into compounds of formula VIII

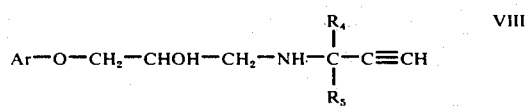

where $R_4$ and $R_5$ are defined as in formula I, and Ar is a group of the partial formula

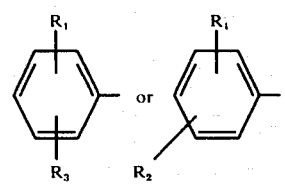

(where $R_1$, $R_2$ and $R_3$ have the above meanings), for example, with a mixture of hydrogen halide and hydrogen peroxide at elevated temperature.

Furthermore, the following process is suitable for producing compounds of general formula I, where $R_1$ and/or $R_2$ represent a -CN:

g. Introducing a -CN group into compound of general formula IXa

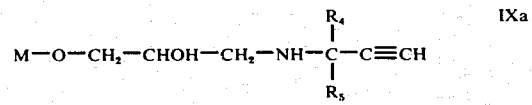

where $R_4$ and $R_5$ are defined as in formula I, and M represents a group of the partial formula

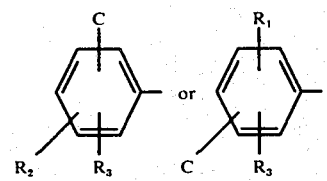

(where $R_1$, $R_2$ and $R_3$ are defined as in formula I) and C is an amino group or halogen.

This may be effected, in case C is an amino group, by means of diazotizing and boiling in the presence of cyanides such as KCN and in case C is halogen by reaction with Cu(I)CN in a high boiling solvent.

The starting compounds required for carrying out the processes (a) to (g) have already been partly known. The remainder can be obtained by known processes. Thus, the epoxides of formula II may be produced easily by reaction with a corresponding phenol or phenolate of formula X

where $R_1$ to $R_3$ have the meanings mentioned above and Kt is hydrogen or a cation (e.g., an alkali metal cation). The epoxides may be used for production of further starting materials; for instance, the halogen hydrins of formula II may be produced by reacting the epoxides with the corresponding hydrogen halide.

Amines of formula III have been known and represent mostly commercial products. Compounds of formula IV may be obtained by reacting a halohydrin of formula II with a compound (such as vinyl ether or dihydropyran) to give the protective group G and, subsequently, reacting the obtained compound of formula

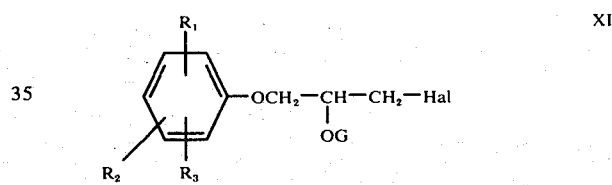

with a compound of general formula III.

The tertiary amines of formula V are obtained by reacting a compound of general formula X with a compound of general formula

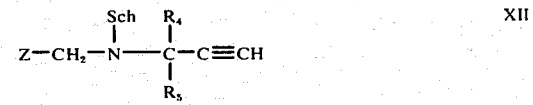

where $R_4$, $R_5$ and Sch have the above-mentioned meanings and Z is a halide.

The oxazolidinones of formula VI (e.g., compounds where X = CO) are producible, for example, starting from the epoxides of formula II, by reacting the latter with a urethane (producible from a chloroethyl formate and an amine of formula II) of formula

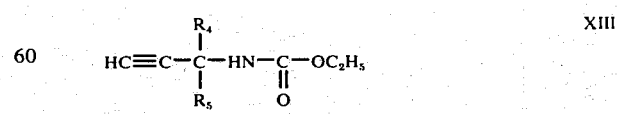

where $R_4$ and $R_5$ have the meanings mentioned above.

The compounds of formulas VIIa, VIIb, VIII, IXa and IXb already contain the complete 1-phenoxy-2-hydroxy-3-alkynylamino-propane structure and may, therefore, be produced analogously to the process (a)

described above, starting from the corresponding phenol, via the corresponding 1-phenoxy-2,3-epoxypropane (producible by reaction with epichlorohydrin) by reaction with an alkynylamine of formula III.

The compounds according to the invention possess an asymmetric carbon atom at the CHOH group and can occur, therefore, as racemates as well as in the form of optical antipodes. The latter may be obtained by separation of racemates with the conventional optically active acids, such as dibenzoyl- (or di-p-toluyl-)D-tartaric acid or D-3-bromocamphor-8-sulfonic acid or by using optically active starting materials as well.

The 1-aryloxy-2-hydroxy-3-alkynylamino-propanes of general formula I according to the invention may be converted into the physiologically compatible acid addition salts thereof in the conventional way. Suitable acids are, for example, hydrochloric acid, hydrobromic acid, sulfuric acid, methane-sulfonic acid, maleic acid, acetic acid, oxalic acid, lactic acid, tartaric acid or 8-chlorotheophylline.

The compounds of general formula I or the physiologically compatible acid addition salts thereof have shown valuable therapeutic properties, in particular, adrenolytic properties as demonstrated by animal tests in guinea pigs and may, therefore, be used for treatment or prophylaxis of diseases of the coronaries and for treatment of cardiac arrhythmia, especially of tachycardia, in human medicine. The blood-pressure decreasing properties of the compounds are therapeutically interesting too. Compared to the known $\beta$-receptor blockers, for example, the commercial product 1-(1-naphthyloxy)-2-hydroxy-3-isopropylaminopropane (Propranolol), the compounds have the advantage of a considerably decreased toxicity combined with a superior action.

The invention, therefore, also relates to a process for the treatment of coronary diseases, cardiac arrhythmia and high blood pressure in warm-blooded animals comprising administering a safe but effective amount of the 1-aryloxy-2-hydroxy-3-alkynylamino-propane compounds of formula I.

Here compounds of general formula I have proved to be valuable, in particular, where $R_4$ and $R_5$ represent each a methyl group and one of $R_1$, $R_2$ and $R_3$ is other than hydrogen (substituted 1-phenoxy-3-(2-methylbutynyl-3-amino-2)-2-propanols).

$R_2$ may represent in this case preferably hydrogen, but furthermore, lower alkyl (e.g., methyl), preferably in the 5-position to the propanolamine side-chain, while $R_3$ is hydrogen as a rule. $R_4$ and $R_5$ are again preferably methyl.

Important individual compounds are, in particular: 1-(2-cyano-phenoxy)-3-(2-methylbutynyl-3-amino-2)-2-propanol and the physiologically compatible acid addition salts thereof.

The single dose of the compounds according to the invention lies at 1 to 300 mg, preferably 5 to 100 mg (orally) or 1 to 20 mg (parenterally). When administered to warmblooded animals, the single dosage is from 0.015 mgm to 5 mgm/kg.

The active ingredients according to the invention may be incorporated into the conventional galenic forms of administration, such as tablets, coated tablets, solutions, emulsions, powders, capsules or forms of sustained release. For the production of the above, the usual pharmaceutical excipients as well as the conventional methods of production may be applied.

Corresponding tablets may be obtained by mixing the active ingredients with known excipients, for example, with inert diluents, such as calcium carbonate, calcium phosphate or lactose, disintegrants, such as corn starch or alginic acid, binders, such as starch or gelatin, lubricants, such as magnesium stearate or talc and/or agents for obtaining sustained release, such as carboxypolymethylene, carboxymethylcellulose, cellulose acetate/phthalate or polyvinylacetate.

The tablets may also be composed of several layers. There may be produced correspondingly coated tablets by means of coating cores, prepared analogous to the tablets, with agents usually applied for tablet-coats, such as polyvinylpyrrolidone or shellac, gum arabic, talc, titanium dioxide or sugar. For obtaining sustained release or in order to avoid incompatibilities, the core may be consist of several layers as well. Thus, the tablet coat for obtaining sustained release may also consist of several layers, whereby the excipients mentioned above for tablets may be used.

Drinks of the active ingredients or active ingredient combinations according to the invention may additionally contain a sweetener, such as saccharin, cyclamate, glycerin or sugar, as well as an agent improving the taste, for example, a flavor, such as vanilla or orange extract. Besides they may comprise suspension auxiliaries or thickeners, such as sodium carboxymethylcellulose, wetting agents, such as condensation products of fatty alcohols with ethylene oxide, or protective substances, such as p-hydroxybenzoates.

Injectable solutions are produced in the conventional way, such as under addition of preservation agents, such as p-hydroxybenzoates, or stabilizers, such as "Komplexonen" (the sodium salt of ethylene diaminetetraacetic acid), and filled into injection vials or ampoules.

Capsules containing the active ingredients or active ingredient combinations may be produced, for example, by admixing the active ingredients with inert carriers, such as lactose or sorbitol, and filling same into gelatin capsules.

Suitable suppositories may be produced by mixing the active ingredients or active ingredient combinations envisaged for same with conventional carriers, such as neutral fats or polyoxyethyleneglycol or its derivatives.

The compounds of the invention are suitable as well for combination with other pharmacodynamically active substances, such as, for example, coronary dilatators, sympathicomimetics, cardiac glycosides or tranquilizers.

The following examples illustrate the preparation of compounds of the formula I.

EXAMPLE 1

1-(2-Cyanophenoxy)-3-(2-methylbutynyl-3-amino-2)-2-propanol · HCl (according to process [a]) (I, $R_1$ = 2-CN, $R_2$ and $R_3$ = H, $R_4$ and $R_5$ = $CH_3$)

17.5 Grams (0.1 mol) of 1-(2-cyanophenoxy)-2,3-epoxypropane were dissolved in 130 ml of ethanol. After addition of 16.6 gm (0.2 mol) of 2-methyl-2-amine-butyne-3, the mixture was refluxed for 2 hours. The solvent was distilled off. The remaining residue was acidified with HCl and shaken. After vacuum filtering the insoluble particles, the filtrate was adjusted alkaline by NaOH. The precipitating base was dissolved in chloroform and the organic phase, after separation, was dried over $Na_2SO_4$. After filtration the chloroform was distilled off and the residue was recrystallized from ethyl acetate under addition of petroleum ether. The base was dissolved in acetonitrile and acidified with alcoholic HCl. The hydrochloride crystallized colorlessly.

Yield: 13.9 gm (uniform substance, in the thin-layer chromatogram). M.p. 169° to 171° C.

EXAMPLE 2

1-(2-Cyanophenoxy)-3-(1-ethynylcyclohexylamino)-2-propanol · HCl (according to process [a]) (I, $R_1$ = 2-CN, $R_2$ and $R_3$ = H, $R_4$ and $R_5$ together = $-(CH_2)_5-$ 9 Grams (0.05 mol) of 1-ethynylcyclohexylamine were dissolved together with 8.7 gm (0.05 mol) of 1-(2-cyanophenoxy)-2,3-epoxypropane in 100 ml of ethanol and refluxed for 2 hours. After having distilled off the solvent, the residue was dissolved in ethyl acetate and shaken with diluted HCl. The aqueous phase was separated and adjusted alkaline with NaOH. The precipitated base was extracted with ethyl acetate. The organic phase was washed, dried over $MgSO_4$, filtered and the solvent was distilled off. The remaining residue was recrystallized from ethyl acetate under addition of ligroin. The colorless crystalline base was dissolved in alcohol. Alcoholic HCl was added and the hydrochloride was brought to crystallization by dropping in ether. After separation, the salt was recrystallized once more from ethanol under addition of ether.

Yield: 6.5 gm, m.p. 176° to 177° C.

Analogous to the Examples 1 and 2, the following compounds of the formula I are produced in line with process (a), e.g. by reacting the correspondingly substituted 1-phenoxy-2,3-epoxypropane according to formula II with the corresponding amine according to formula III in ethanol.

TABLE

| $R_1$ | $R_2$ | $R_3$ | $R_4$ | $R_5$ | M.P. of HCl-Salt in Case Nothing Else Indicated °C |
|---|---|---|---|---|---|
| 2-CN | H | H | $C_2H_5$ | $C_2H_5$ | 170–171 |
| 4-CN | H | H | $CH_3$ | $CH_3$ | 194–196 |
| 4-NH-CO-NHC$_2$H$_5$ | 2-CN | H | $CH_3$ | $CH_3$ | 161–164 (Base) |
| 4-NH-CO-NHCH$_3$ | 2-CN | H | $CH_3$ | $CH_3$ | 155–157 (Base) |
| 4-NH-CO-NHiC$_3$H$_7$ | 2-CN | H | $CH_3$ | $CH_3$ | 127–130 (Base) |
| 2-CN | 4-Cl | H | $CH_3$ | $CH_3$ | 176–177 |

EXAMPLE 3

1-(2-Cyanophenoxy)-3-(2-methylbutyne-3-amino-2)-2-propanol · HCl (according to process [d]) (I, $R_1$ = 2-CN, $R_2$ and $R_3$ = H, $R_4$ and $R_5$ = $CH_3$)

2.84 Grams (0.01 mol) of 3-(2-methylbutyne-3-yl-2)-5-(2-cyanophenoxymethyl)-oxazolidine-2-one were refluxed in 20 ml of ethanol, after addition of 3 gm of KOH in 6 ml of water, for 3 hours. After having distilled off the solvent, the residue was treated with water and extracted with chloroform. Then the chloroform solution was shaken with diluted HCl and the separated aqueous phase was adjusted alkaline with NaOH. The precipitating base was taken up in chloroform. The organic phase was washed with water and dried over $Na_2SO_4$. After filtration, $CHCl_3$ was distilled off and the residue was recrystallized from ethyl acetate under addition of petroleum ether.

Yield: 1.3 gm, m.p. 84° to 86° C (base). Mixed melting point with identical substance; 83° to 85° C.

EXAMPLE 4

1-(2-Cyano-4-chlorophenoxy)-3-(2-methylbutynyl-3-amino-2)-2-propanol · HCl (according to process [f]) (I, $R_1$ = 2-CN, $R_2$ = 4-Cl, $R_3$ = H, $R_4$ and $R_5$ = $CH_3$)

3.87 Grams (0.015 mol) of 1-(2-cyanophenoxy)-3-(2-methylbutynyl-3-amino-2)-2-propanol were admixed with 25 ml of conc. HCl and heated to 45° C. While cooling, 1.7 gm (0.015 mol) of 30% $H_2O_2$ were dropped in in such a way that the temperature did not rise above 65° C. After the batch had been stirred for a further 30 minutes, the crystal mass was vacuumed off and washed with water. The hydrochloride was recrystallized from ethanol.

Yield: 1.95 gm, m.p. 176° to 177° C.

EXAMPLE 5

1-(2-Cyanophenoxy)-3-(2-methylbutynyl-3-amino-2)-2-propanol · HCl (according to process [g]) (I, $R_1$ = 2-CN, $R_2$ and $R_3$ = H, $R_4$ and $R_5$ = $CH_3$)

0.697 Gram (0.002 mol) of 1-(2-bromophenoxy)-3-(2-methylbutynyl-3-amino-2)-2-propanol hydrochloride were admixed with 0.376 gm (0.0042 mol) of Cu(I)CN and 0.4 gm of dimethylformamide and heated for 2 hours to 190° C. After cooling, the mixture was treated with water and adjusted alkaline with NaOH. The basic portions were taken up in $CHCl_3$ and washed with water. The chloroform was distilled off and the residue was purified through a silica gel column. The pure base thus obtained was dissolved in acetonitrile and acidified with alcoholic HCl. The hydrochloride crystallized colorlessly. M.p. 168° to 171° C.

EXAMPLES OF FORMULATIONS

1. Tablets

| | |
|---|---|
| 1-(2-cyanophenoxy)-3-(2-methyl-butynyl-3-amino-2-)-2-propanol . HCl | 40.0 parts |
| Corn starch | 164.0 " |
| Sec. calcium phosphate | 240.0 " |
| Magnesium stearate | 1.0 " |
| | 445.0 parts |

Production:

The individual components were admixed well and the mixture was granulated in the usual way. The granulate was pressed into tablets of 445 mgm by weight, of which each contains 40 mgm of active ingredient.

Instead of the active ingredients mentioned in this example, the substances 1-(2-cyanophenoxy)-3-(1-ethynylcyclohexylamino)-2-propanol · HCl and 1-(2-cyano-4-chlorophenoxy)-3-(2-methylbutynyl-3-amino-2)-2-propanol may be used in the same quantity.

2. Gelatin Capsules

The content of the capsules was composed as follows:

| | |
|---|---|
| 1-(2-cyanophenoxy)-3-(2-methyl-butynyl-3-amino-2)-2-propanol . HCl | 25.0 parts |
| Corn starch | 175.0 parts |

-continued

| | 200.0 parts |
|---|---|

Production:

The active ingredients of the content of capsule were mixed well and 200 mg portions of the mixture were filled into gelatin capsules of suitable size. Each capsule contains 25 mg of the active ingredient.

3. Injection Solution

The solution was produced of the following ingredients:

| 1-(2-cyano-5-methylphenoxy)-3-(2-methylbutynyl-3-amino-2)-2-propanol . HCl | 2.5 parts |
|---|---|
| Sodium salt of EDTA (ethylenediaminetetraacetic acid) | 0.2 parts |
| Distilled water ad | 100.0 parts |

Production:

The active ingredient and EDTA-salt were dissolved in sufficient water and filled with water to the desired volume. The solution was filtered free from suspended particles and filled into ampoules under aseptic conditions. Finally, the ampoules were sterilized and sealed. Each ampoule contains 25 mg of active ingredient.

4. Coated Tablets with Sustained Release

Core:

| (-)-1-(2-cyanophenoxy)-3-(2-methylbutynyl-3-amino-2)-2-propanol . HCl | 25.0 parts |
|---|---|
| Carboxymethyl cellulose (CMC) | 295.0 " |
| Stearic acid | 20.0 " |
| Cellulose acetate/phthalate (CAP) | 40.0 " |
| | 380.0 parts |

Production:

Active ingredient, CMC and stearic acid were mixed well and the mixture was granulated in the usual way, using a solution of the CAP in 200 ml of a mixture of ethanol/ethyl acetate. Then the granulate was pressed to 380 mg cores, coated in the conventional way with a sugary 5% solution of polyvinylpyrrolidone in water. Each coated tablet contains 25 mg of active ingredient.

5. Tablets

| 1-α-Naphthoxy-3-(3-ethylpentynyl-4-amino-3)-2-propanol . HCl | 35.0 gm |
|---|---|
| 2,6-bis-(diethanolamino)-4,8-dipiperidinopyrimido-[5,4-d]-pyrimidine | 75.0 gm |
| Lactose | 164.0 gm |
| Corn starch | 194.0 gm |
| Colloidal silicic acid | 14.0 gm |
| Polyvinylpyrrolidone | 6.0 gm |
| Magnesium stearate | 2.0 gm |
| Soluble starch | 10.0 gm |
| | 500.0 gm |

Production:

The active ingredient together with the lactose, corn starch, colloidal silicic acid and polyvinyl pyrrolidone was granulated after thorough mixing in the usual way, using an aqueous solution of the soluble starch. The granulate was admixed with the magnesium stearate and pressed into 1000 tablets each of 500 mgm of weight, containing each 35 mgm of the first and 75 mgm of the second active ingredient.

The preceding specific embodiments are illustrative of the practice of the invention. It is to be understood, however, that other expedients known to those skilled in the art or disclosed herein may be employed without departing from the spirit of the invention and the scope of the appended claims.

We claim:

1. A pharmaceutical dosage unit composition consisting essentially of an inert pharmaceutical carrier and an effective adrenolytic or hypotensive amount of a racemic or optically active compound of the formula

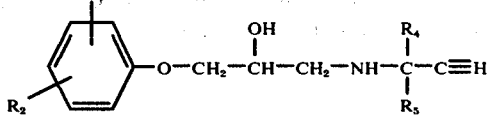

wherein $R_1$ is $-(CH_2)_x-CN$, where X is 0, 1, 2 or 3, $R_2$ is hydrogen, halogen or $-NH-CO-NHR$, where R is lower alkyl, $R_4$ is alkyl of 1 to 3 carbon atoms, and $R_5$ is alkyl of 1 to 3 carbon atoms or, together with $R_4$, $-(CH_2)_p-$ where p is 4, 5 or 6, or a physiologically compatible acid addition salt thereof.

2. The composition of claim 1, where $R_1$ is $-(CH_2)_x-CN$, where X is 0, 1, 2 or 3, $R_2$ is hydrogen, halogen or $-NH-CO-NHR$, where R is lower alkyl, and $R_4$ and $R_5$ are methyl.

3. The composition of claim 1, where said compound is of the formula

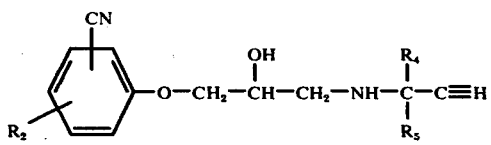

wherein $R_2$ is hydrogen, chlorine or $-NH-CO-NHR$, where R is alkyl of 1 to 3 carbon atoms, and $R_4$ and $R_5$ are methyl, ethyl or together pentamethylene, or a physiologically compatible acid addition salt thereof.

4. The composition of claim 3, where $R_2$ is hydrogen, chlorine or $-NH-CO-NHR$, where R is alkyl of 1 to 3 carbon atoms, and $R_4$ and $R_5$ are methyl.

5. The composition of claim 3, where said compound is of the formula

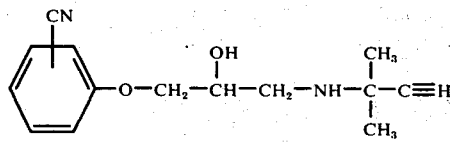

or a physiologically compatible acid addition salt thereof.

6. The composition of claim 3, where
 $R_1$ is 2-cyano,
 $R_2$ is hydrogen, and
 $R_4$ and $R_5$ are methyl.

7. A method of inhibiting the action of adrenergic nerves or lowering the blood pressure in a warmblooded animal in need of such treatment, which comprises administering to said animal an effective adrenolytic or hypotensive amount of a racemic or optically active compound of the formula

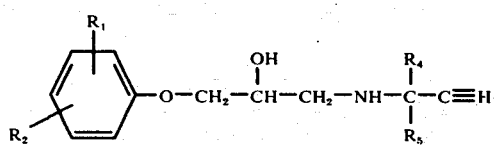

wherein
 $R_1$ is —$(CH_2)_X$—CN, where X is 0, 1, 2 or 3,
 $R_2$ is hydrogen, halogen or —NH—CO—NHR, where R is lower alkyl,
 $R_4$ is alkyl of 1 to 3 carbon atoms, and
 $R_5$ is alkyl of 1 to 3 carbon atoms or, together with $R_4$, —$(CH_2)_p$— where p is 4, 5 or 6,
or a physiologically compatible acid addition salt thereof, 8. The method of claim 7, where
 $R_1$ is —$(CH_2)_X$—CN, where X is 0, 1, 2 or 3,
 $R_2$ is hydrogen, halogen or —NH—CO—NHR, where R is lower alkyl, and
 $R_4$ and $R_5$ are methyl.

9. The method of claim 7, where said compound is of the formula

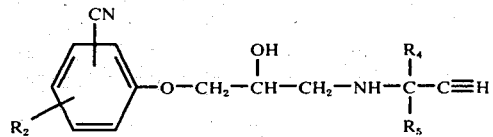

wherein
 $R_2$ is hydrogen, chlorine or —NH—CO—NHR, where R is alkyl of 1 to 3 carbon atoms, and
 $R_4$ and $R_5$ are methyl, ethyl or together pentamethylene,
or a physiologically compatible acid addition salt thereof.

10. The method of claim 9, where
 $R_2$ is hydrogen, chlorine or —NH—CO—NHR, where R is alkyl of 1 to 3 carbon atoms, and
 $R_4$ and $R_5$ are methyl.

11. The method of claim 9, where said compound is of the formula

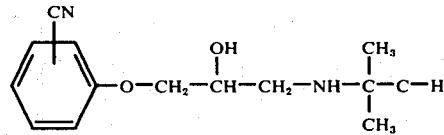

or a physiologically compatible acid addition salt thereof.

12. The method of claim 9, where
 $R_1$ is 2-cyano,
 $R_2$ is hydrogen, and
 $R_4$ and $R_5$ are methyl.

* * * * *